(12) United States Patent
Colditz

(10) Patent No.: US 6,702,772 B1
(45) Date of Patent: Mar. 9, 2004

(54) THUMB CMC RESTRICTION SPLINT

(76) Inventor: Judy C. Colditz, 2619 London Dr., Raleigh, NC (US) 27608

( * ) Notice: Subject to any disclaimer, the term of this patent is extended or adjusted under 35 U.S.C. 154(b) by 0 days.

(21) Appl. No.: 09/799,958

(22) Filed: Mar. 6, 2001

Related U.S. Application Data

(60) Provisional application No. 60/187,286, filed on Mar. 6, 2000.

(51) Int. Cl.$^7$ .................................................. A61F 5/00
(52) U.S. Cl. ............................... 602/22; 602/20; 602/21; 602/60; 602/62; 602/64
(58) Field of Search ................................ 602/5, 20–22, 602/23, 1, 12, 60–62, 64; 2/16, 21, 455–456; 128/845–846, 869, 878–879

(56) References Cited

U.S. PATENT DOCUMENTS

| | | | |
|---|---|---|---|
| 5,513,657 A | * | 5/1996 | Nelson .......................... 128/879 |
| 5,526,531 A | * | 6/1996 | Olson et al. ...................... 2/16 |
| 5,649,900 A | * | 7/1997 | Kline |
| 5,759,166 A | * | 6/1998 | Nelson |
| 5,928,172 A | * | 7/1999 | Gaylord ........................ 602/21 |
| 6,101,628 A | * | 8/2000 | Earl ................................ 2/21 |
| 6,196,985 B1 | * | 3/2001 | Slautterback ................ 602/20 |

* cited by examiner

*Primary Examiner*—Nicholas D. Lucchesi
*Assistant Examiner*—Lalita M. Hamilton
(74) *Attorney, Agent, or Firm*—Mills Law Firm PLLC

(57) ABSTRACT

A restriction splint for immobilizing the CMC joint of a hand includes a splint body of a soft stretchable material that overlies the dorsum and palm of the hand and a tensioning strap having one end connected to the splint body at the dorsum and a free end wrapping around the CMC joint capsule, extending through the web between the thumb and the index finger and releasably connected to the splint body under extension for orienting and immobilizing the thumb without consequent loss of hand functioning.

16 Claims, 5 Drawing Sheets

THUMB CMC RESTRICTION SPLINT

RELATED APPLICATION

This application claims the benefit under 35 USC 121 of U.S. provisional application Ser. No. 60/187,286 filed on Mar. 6, 2000 in the name of Judy C. Colditz and entitled "Method and Apparatus for a Thumb CMC Restriction Splint".

FIELD OF THE INVENTION

The present invention relates to a medical apparatus and method for joint immobilization, and, in particular, to a method and apparatus for immobilizing the thumb CMC joint to eliminate pain.

The thumb trapeziometacarpal joint, also call the thumb carpometacarpal joint (CMC joint), is the most common site in the upper extremity of the human body for surgery due to disabling osteoarthritis, which is particularly prevalent in postmenopausal women, many of whom already have laxity of the joint. Osteoarthritis causes increased laxity of the thumb CMC joint capsule, creating a common clinical complaint of pain upon resistive thumb motion, such as experienced during forceful pinching.

Immobilization splinting is used by most surgeons and therapists as part of a conservative, non-surgical treatment for painful thumb CMC joints. Typical immobilization splint involve one and often both adjacent joints. Such comprehensive immobilization results in poor patient compliance and limitation of hand function, both of which appear to be related to the number of immobilized joints. Immobilization of the thumb MP joint limits flexion. Extension and abduction/adduction. Immobilization of the wrist demands greater range of proximal joint, making function more demanding. Accordingly, the patient must choose the benefits of compliance against the loss of functional use through immobilization.

It would therefore be a significant advance in the art, and is accordingly an object of the present invention, to reduce the number of joints adjacent the thumb CMC joint that must be immobilized, in addition to the thumb CMC joint, to reduce pain and increase compliance. A further object of the present invention is to reduce the size of the splint for immobilizing the thumb CMC joint for affording greater comfort for the patient lessening interference with functionality thereby increasing patient compliance.

SUMMARY OF THE INVENTION

The foregoing objects are accomplished by a novel thumb CMC joint splint for reducing joint pain without loss of hand functionality thereby increasing patient compliance. In certain prior splint designs, rigid custom molded thermoplastic splints have been employed immobilizing the joint and wrist. Other designs have employed non-rigid materials, such as leather or fabric, that encompass the thumb and wrist joints to provide global support therefor. In a preferred embodiment of the present invention, the splint comprises an adjustable wrist band, formed of a soft good such as neoprene laminated with a cloth knit, having a dorsal flap that overlies the side and bottom of the CMC capsule. An elongated tensioning strap is attached at one end to the top surface of the wrist band and is tensioned over the dorsal flap and attached thereto at a first attachment location to provide peripheral support at the capsule. The tensioning strap extends forwardly around the capsule and extends rearwardly over the web between the thumb and the first finger with the distal end tensioned and releasably connect to the wrist band at a second attachment location thereby outwardly spacing the thumb and immobilizing the CMC joint, without loss of thumb or adjacent joint functionality.

DESCRIPTION OF THE DRAWINGS

The above and other objects and advantages of the present invention will become apparent upon reading the following detailed description taken in conjunction with the accompanying drawings in which.

DETAILED DESCRIPTION OF THE PREFERRED EMBODIMENTS

Figure 5:
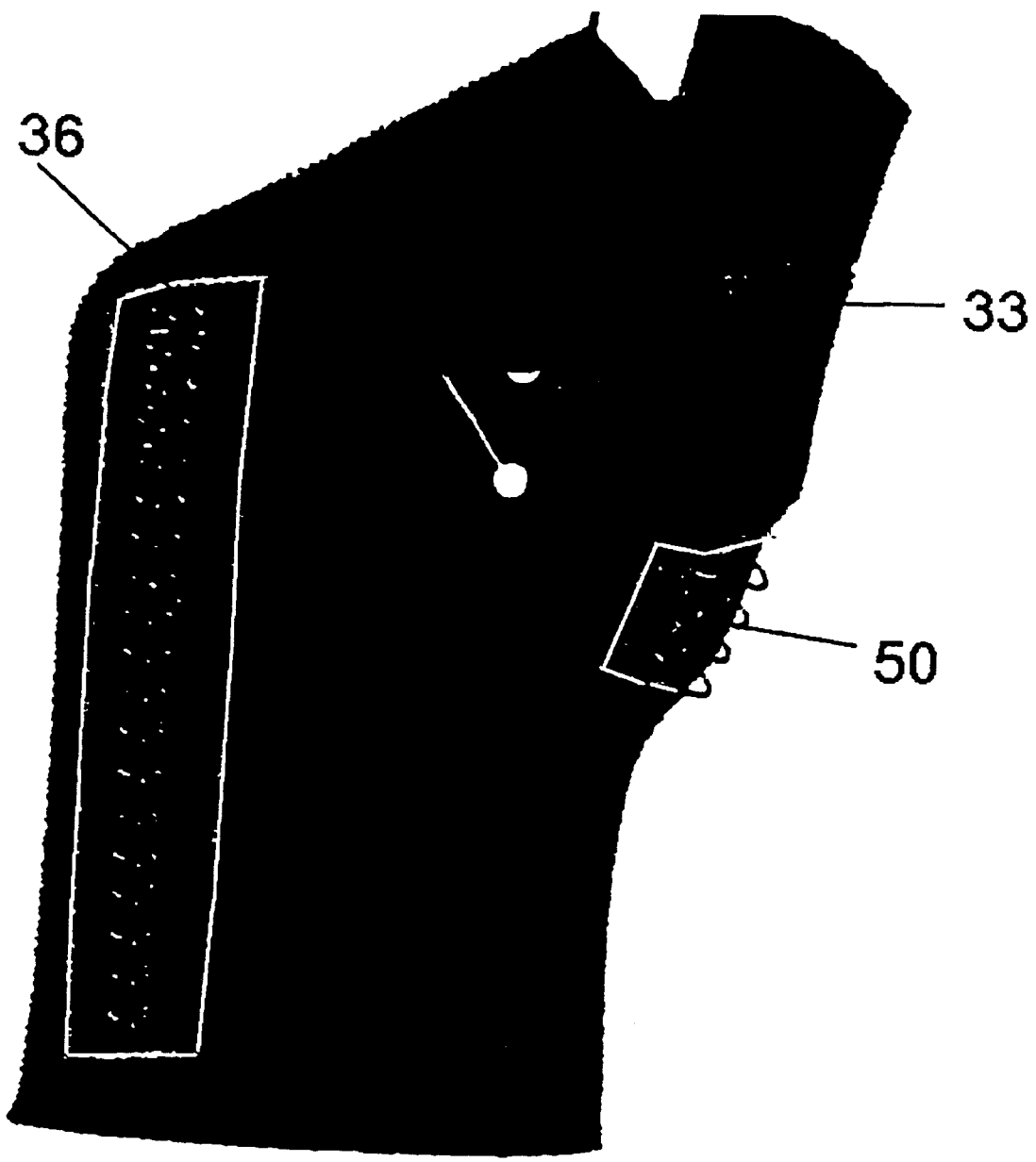
FIG. 5 is a bottom view of the restriction splint.

Referring to the drawings for the purpose of describing the preferred embodiment and not for limiting same, FIG. 5 illustrates a thumb CMC restriction splint 10 worn by a patient for supporting and providing light compression of the CMC joint for alleviating arthritic pain and instability, and the discomfort associated with repetitive motion. In the illustrated immobilized position, it will be appreciated that the splint is disposed forwardly of the wrist of the patient and immobilizes the thumb slightly outwardly of the hand while providing compressive peripheral support for the CMC joint capsule.

Figure 2:
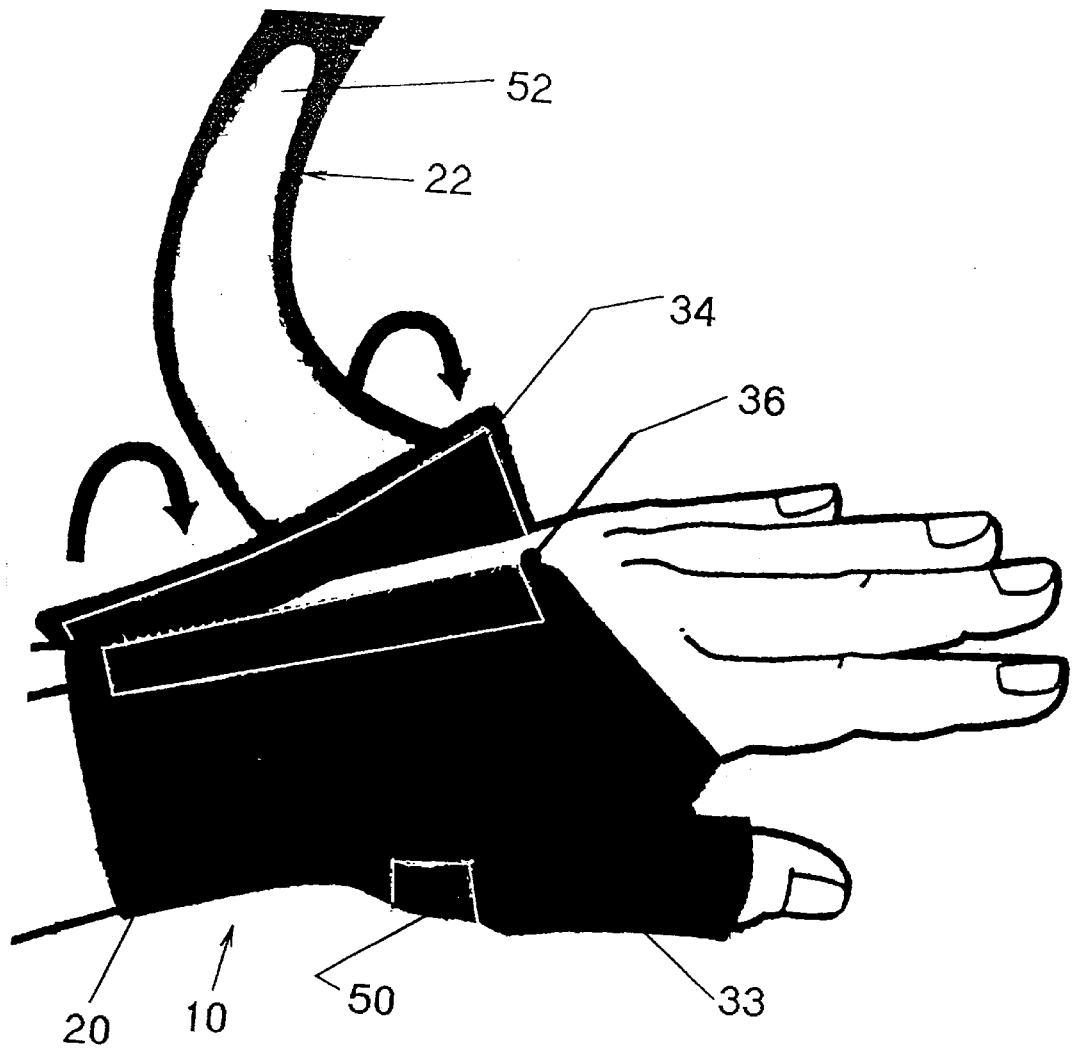
FIG. 2 is an illustration of the restriction splint on the hand of a patient in the preparatory position.
Figure 3:
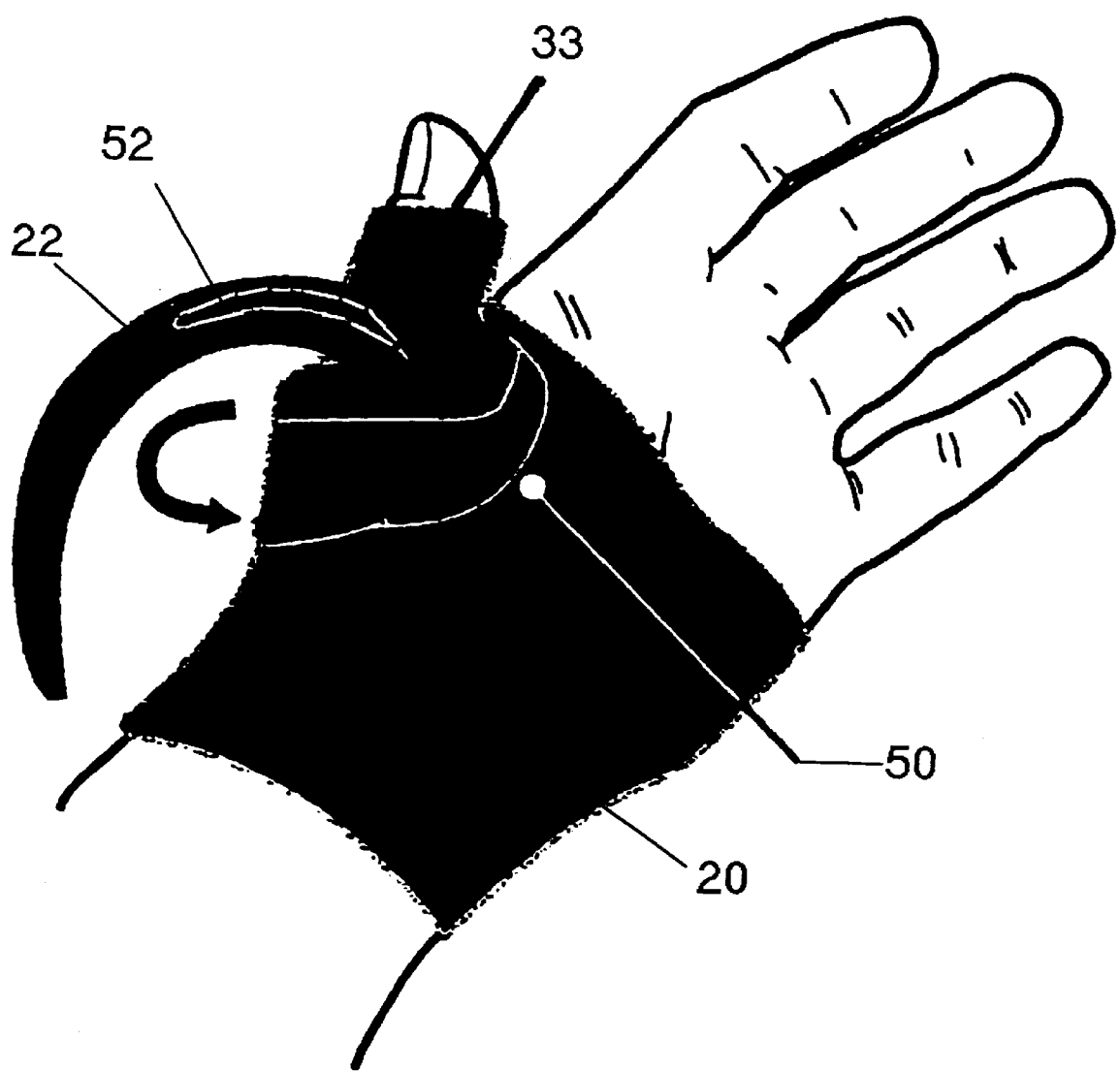
FIG. 3 is an illustration of the restriction splint in the partially immobilized position.

The splint 10 comprises a splint body 20 disposed around the wrist of the patient and a CMC tensioning strap 22 attached at one end to the splint body 20 and wrapped around the base of the thumb and through the web between the thumb and the hand with a free end 24 releasably attached to the strap 22 adjacent the splint body 20, as shown in FIGS. 2 and 3.

It will be appreciated that the splint 10 as applied interfaces with various muscles and joints in the hand. There are four intrinsic thenar muscles: the adductor pollicis ("AP"), the flexor pollicis brevis ("FPB"), the opponens pollicis ("OP"), and the abductor pollicis brevis ("APB"). The FPB flexes the first metacarpal across the palm and the APB pulls the metacarpal into palmar abduction. Both the OP and the AP are larger muscles than the FPB and APB, with the OP inserting along the length of the first metacarpal and the AP originating along the length of the third metacarpal. The AP brings the first metacarpal toward the second metacarpal. The OP rotates the first metacarpal as the entire thumb reaches toward a fingertip. All of these muscles contract to stabilize the CMC and MP joints during pinch so the force of the flexor pollicis longus can be transmitted distally. Because the insertion of the AP, FPB, and APB are distal to the thumb MP joint, these muscles have a long moment arm to effect CMC joint motion. The long insertion of the OP on the first metacarpal allows this muscle to effectively move the CMC joint.

The antagonistic muscles, however, are extrinsic muscles with weaker mechanical advantage. Originating on the radius and ulna in the forearm, the APL inserts on the base of the first metacarpal. Because the tendon insertion is close to the axis of the joint, it provides little mechanical advantage for extension at the CMC joint. The extensor pollicis brevis ("EPB") originates on the interosseus membrane and the radius in the forearm and inserts just beyond the thumb MP joint into the base of the thumb proximal phalanx. It primarily extends the thumb MP joint and secondarily extends/abducts the thumb CMC joint. Only when the MP joint of the thumb is fully extended does it then effectively act on the CMC joint. The extensor pollicis longus ("EPL") originates in the forearm from the interosseus membrane and ulna. inserting at the base of the distal phalanx. Crossing over all three thumb joints, the EPL can assist in the CMC joint extension only after it has exhausted its excursion at the other joints. Thus, the APL, EPB, and EPL muscles are relatively inefficient extensors and abductors at the CMC joint, in contrast to the more efficient intrinsic thenar muscles that primarily flex and adduct/abduct the thumb CMC joint. With three of the four thenar muscles (FPB, OP, and AP) pulling the first metacarpal head toward the palm (into flexion), the balance of motion at the thumb CMC appears to be leaded toward flexion. As osteoarthritis develops, the already slack capsule of the thumb CMC joint becomes attenuated. The weaker dorsal fibers of the trapeziometacarpal capsule allows the base of the first metacarpal to sublux dorsally. As the intrinsic thenar muscles pull on the distal end of the first metacarpal, it flexes forward, levering the metacarpal. It is postulated that during pinch, when the thenar muscles contract, the first metacarpal tilts; i.e., the distal end moves toward the palm and the proximal end shifts dorsally. It is this shift of motion, even though perhaps slight, that appears to create pain. It will thus be appreciated that the restriction splint 10 will effectively prevent the first metacarpal tilting motion, thereby controlling pain during thumb use.

The splint body 20 is generally rectangular and is applied around the wrist over the dorsum, around the CMC joint, and over the base of the palm. The splint body 20 has a length greater than the wrist of the patient with the free end 30 and the strap end 32 in overlapping relationship over the dorsum. The splint body includes an open ended thumb sleeve 33 at the forward end thereof through which the thumb of the patient extends. The free end 30 and the strap end 32 are adjustably releasably attached at a first hook and loop attachment site comprising a rectangular hook pad 34 attached to the outer surface of the free end 30, and a corresponding rectangular loop pad 30 sewn to the inner surface of the strap end 32. Accordingly, the patient preferably applies the splint body 20 with light tensioning whereby the outer portion of the body 20 compressively engages the CMC capsule site.

The tensioning strap 22 is attached at one end to the splint body 20 at the free end 30 at a longitudinal seam 40. The tensioning strap 22 is an elongated body having a generally rectangular base 42 and an arcuate outwardly tapering body 44 extending forwardly of the splint body in assembly.

Figure 4:
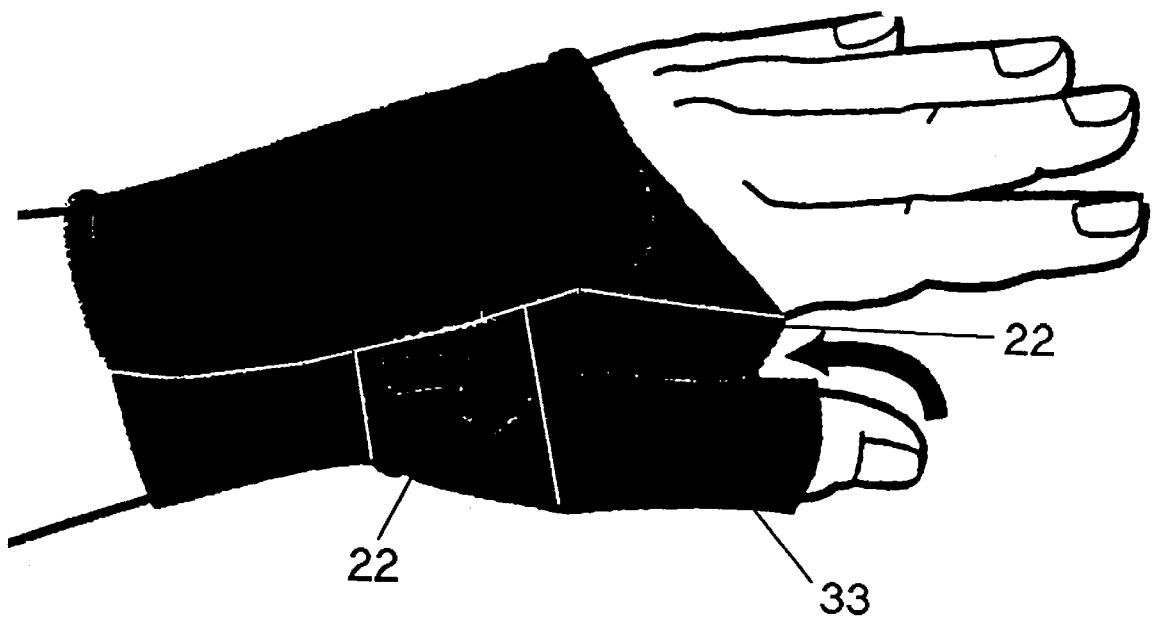
FIG. 4 is an illustration of the restriction splint in the immobilized position.

The tensioning strap 22 is intermediately releasably attached to the splint body 20 as a CMC attachment site at a second hook and loop fastening interface comprising a curved hooked pad 50 attached to the outer surface of the splint body 20 overlying the CMC joint and to a correspondingly curved loop pad 52 attached to the inner surface of the tensioning strap 22. As shown in FIG. 4, the tensioning strap 22 is initially applied by slight extension at attachment of the hooked pad 50 to the loop pad 52 at the CMC attachment site. This intermediate attachment prevents movement of the strap relative to the splint body 20 during functional hand movement while maintaining a compressive interface at the CMC joint. The curved free end of the tensioning strap 22 is configured to conformably wrap around the base of the thumb and extend rearwardly through the web between the thumb and the hand terminating adjacent the base of the tensioning strap 22. The free end of the tensioning strap 22 is tensioned and releasably attached to the splint 10 at a third hook and loop attachment site at the base of the strap comprising hook pad 60 attached to the outer surface of the strap at the base adjacent the strap end of the splint body, and a corresponding loop pad 62 on the inner surface of the free end of the tensioning strap 22 as shown in Figure in FIG. 5.

It will thus be appreciated that the splint 10 as applied to the hand provides a compressive biasing to the thumb that effectively immobilizes the CMC joint, without affecting the functioning of adjacent joints.

Figure 1:
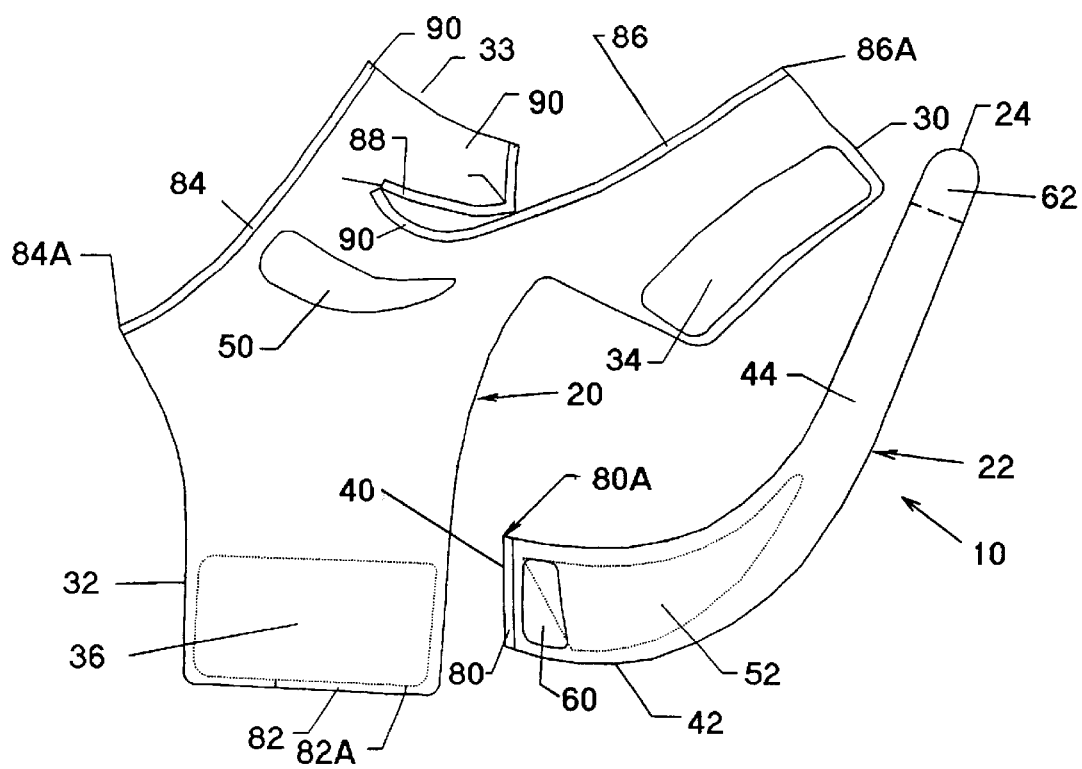
FIG. 1 is a plan view of a pattern for a thumb CMC restriction splint in accordance with a preferred embodiment of the present invention.

Referring to FIG. 1 showing a planar pattern used for fabrication, the preferred embodiment of the thumb CMC restrictive splint 10 is formed from 1/16" perforated elastic neoprene material. Neoprene is equally stretchable in all directions except in specific areas where hook or loop pads are permanently affixed to the material, thereby limiting stretch in those areas. The inner surface of the splint body 20, particularly the palmar portion of the hand, is covered with a suitable terry cloth material to afford better comfort for the patient thereby promoting greater patient compliance. The dorsal portion of the splint body 20 may comprise only the perforated neoprene material. The CMC strap 22 is formed into a generally tapered arcuate shaper for conforming with and providing a lifting action for immobilizing the thumb CMC joint. The strap 22 is fabricated from the same neoprene material as the splint body 20. The CMC strap 22 is curved throughout its length, with its width at the proximal end being approximately ⅔ the length of the patient's first metacarpal decreasing at the distal and to approximately ¼ the length of the patient's first metacarpal. The surface of CMC strap underside portion is the normal cellular surface of neoprene while the outer surface is the normal dense surface of neoprene.

The order in which the attachment and support sites are connected to each other is determined by manufacturing convenience and efficiency. The sequence described herein is for illustrative purposes and is not to be considered a limitation on the manner or method of making the splint 10. Some operations may be performed simultaneously with others. The CMC strap 22 is joined with splint body 20 by abutting first CMC strap fastening surface 80 with second CMC strap fastening surface 82 such that first CMC strap alignment point 80A aligns with second CMC strap alignment point 82A and applying a fastening means across the intersection created by the abutment of fastening surfaces 80A and 82A. In the preferred embodiment, the fastening means is conventional stitching with a durable thread. Other fastening means now or hereafter available may be used to join surfaces of or attach elements to splint 10.

The splint body 201 is partially defined by abutting and applying a suitable fastening means, such as stitching, across the intersection created by the abutment of third splint body fastening surface 88 and fourth splint fourth splint fastening surface 90. In the preferred embodiment, the fastening means is first applied to the abutted edges starting at the junction 92 of third splint body fastening surface 88 and fourth splint body fastening surface 90 and continuing the fastening process along the full length of third splint body fastening surface 88.

The thumb sleeve 33 is defined by abutting first thumb opening fastening surface 84 to second thumb opening fastening surface 86 such that first thumb opening alignment point 86A aligns with second thumb opening alignment point 84A. It should be noted that second thumb opening alignment point is located a distance from thumb opening that is the same as the width of first thumb opening fastening surface such that when first and second thumb opening fastening surfaces are joined, the resulting thumb opening is approximately circular. First thumb opening fastening surface is thereafter joined to second thumb opening fastening surface by a fastening means, such as stitching, across the intersection created by the abutment of the two fastening surfaces thereby defining thumb opening.

The splint body 20 is further defined by abutting first splint body fastening surface 84 to second splint body fastening surface 86 such that second splint body alignment point 86 A aligns with first splint body alignment point 84A and thereafter applying a fastening means, such as stitching, across the intersection created by the abutment of the two fastening surfaces.

The dorsal loop pad 34 is located on palmar portion of splint body 20 adjacent to second CMC strap fastening surface 82 on first wrist end 30 to receive dorsal hook pad 34, located on dorsal portion of splint body 20 opposite second splint body fastening surface 86 on second wrist end 32. To begin using splint 10, a patient inserts her thumb into thumb sleeve 33, positions first end on the body on the dorsum of her hand, folds second end around her hand such that ends overlap, allowing dorsal loop pad 34 to receive and removably adhere to dorsal hook pad 36. Once splint body 20 is properly wrapped about the patient's hand, CMC strap 22 is firmly pulled from the dorsum of the hand, around the radial aspect of the base of the first metacarpal, continues across the palmar aspect of the first metacarpal where CMC hook pad 52 receives and removably adheres to CMC strap loop pad 50, through the web between the patient's thumb and index finger, to the dorsum of the hand where CMC strap underside portion 62, which comprises the cellular surface of neoprene in the preferred embodiment, is received by and removable adhered to CMC strap hook pad 60.

Immobilization of the thumb MP and/or wrist joints as well as the thumb CMC joint effective eliminate pain at the thumb CMC joint. The difficulty in effectively immobilizing the first metacarpal without including other joints is the inability form splinting material circumferentially around the first metacarpal. CMC strap 22 prevents the distal end of the metacarpal from tilting toward the ulnar border of the hand during pinch. CMC joint motion is blocked, and the flexion force can only be transmitted more distally across the MP and IP joints. The lifting action of CMC strap 22 is effective because of thenar muscle contraction. With the present invention properly applied to the patient's hand, the thenar muscles cannot expand out toward the environment as they contract. Their expansion force is directed backward toward the first metacarpal, thereby stabilizing it. This muscle contraction supports the distal end of the metacarpal from flexing forward. This pseudo-hydraulic environment of muscle contraction within a closed space is recognized as the primary principle behind long bone fracture stabilization with functional fracture braces.

As the thumb CMC joint subluxes dorsally, the mechanics of the thumb are altered, changing the balance of forces that cross the thumb MP joint. A modified pull on the thumb MP joint creates secondary problems of balance at this joint. Subluxation of the thumb CMC joint may lead to secondary radial deviation deformity of the thumb MP joint due to an adduction contracture of the first metacarpal. Alternatively, a hyperextension deformity of the thumb MP joint may develop as the flexion/adduction of the first metacarpal allows a straighter line of pull of the EPB that inserts just distal to the MP joint.

Early stabilization of the thumb CMC joint with splint 10 allows maintenance of the normal mechanics across the MP joint. If the imbalance has already begun, an extension of the splint dorsally over the thumb MP joint to block it in mild flexion can alter the pattern of motion during pinch, slowing a further progression of this deformity. The splint 30 leaves the patient's critical digital sensory input unimpeded, is not an impediment during pinching, fingering, or handling activities, and may also be used without impairing gripping activities.

Pressure over the proximal end of the dorso-radial aspect of the first metacarpal should be minimal. The goal is to conform the splinting material snugly around the entire thumb base, not to apply force to attempt reduction of subluxation. It appears that it is the prevention of motion at this joint during pinch, rather than the application of force to attempt to reduce subluxation, that reduces pain. Pressure that attempts to reduce the joint can actually exacerbate the pain. Even patients with grossly dislocated CMC joints can receive benefit from splint 10, because it is the elimination of motion at this joint and not the alignment of the joint that reduces pain. Although application of a splinting device will not in any way remediate the problem, the support of splint 10 during thumb use will reduce pain.

The combination of the predetermined curved shape of CMC strap 22 and the tension resulting from stretching of the elastic neoprene material causes the novel thumb CMC joint lifting action of the present invention to provide thumb CMC joint support and/or light compression for CMC joint arthritis or instability, or for discomfort associated with repetitive motion. Continued stretching of CMC strap 22 around the base of the thumb and a engagement of CMC strap 22 with CMC strap hook pad further increases the resulting lifting action and relief provided to the patient and secures CMC strap distal end 24 such splint 10 is comfortable to wear and conforms to the shape of the patient's hand.

The thumb CMC restrictive splint must be sized according to the patient's hand size. The present embodiments of the invention are manufactured in sizes indicated in the chart below:

| SIZE | CIRCUMFERENCE AT MP JOINTS |
| --- | --- |
| Small | 6.5" to 7" |
| Medium | 7" to 8" |
| Large | 8" to 9" |
| Extra Large | 9: to 10" |

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the sprit and scope of the present invention. The disclosures and description herein are intended to be illustrative and are not in any sense limiting of the invention, which is defined solely in accordance with the following claims.

What is claimed:

1. A restriction splint for immobilizing the CMC joint on the hand of a patient, comprising: body means in the form of a splint body configured for overlying the dorsum and palm of the hand in an operative position, said splint body having a first end for engaging the dorsum and a second end for overlapping said first end, said splint body having a middle portion configured for engaging the CMC capsule of the hand in the operative position; first releasable attaching means for connecting said first end and said second end in said operative position such that said middle portion compressively engages said CMC capsule; first tensioning means in the form of an elongated tensioning strap connected at one end to said second end of said splint body and configured for wrapping around said middle portion of said splint body, said tensioning strap having a free end for extending over the web between the thumb in the operative position and the index finger of the patient and outwardly spacing the thumb from the index finger; second releasable attaching means for connecting an intermediate portion of said strap and said middle portion of said splint body for preventing relative movement therebetween in said operative position; and third releasable attaching means for connecting said free end of said strap adjacent said second end of said splint body in said operative position whereby said tensioning strap inhibits movement of the CMC joint in said operative position.

2. The restriction splint as recited in claim 1 wherein said third releasable means connect said free end of said strap to the exterior of said one end thereof.

3. The restriction splint as recited in claim 1 wherein the width of said strap adjacent the web of the hand positions said thumb at a predetermined orientation with respect to the index finger of the patient.

4. The restriction splint as recited in claim 3 wherein said tensioning straps is formed of a bidirectionally stretchable material.

5. The restriction splint as recited in claim 4 wherein said material is neoprene.

6. The restriction splint as recited in claim 5 wherein said splint body is formed of a bidirectionally stretchable material.

7. The restriction splint as recited in claim 6 wherein said material is neoprene.

8. The restriction splint as recited in claim 6 wherein an absorbent material is attached to the inner surface of said splint body.

9. The restriction splint as recited in claim 4 wherein said releasable attaching means limits the stretch of said material.

10. The restriction splint as recited in claim 1 wherein at least on of said releasable attaching means is a hook and loop fastener.

11. The restriction splint as recited in claim 10 wherein said second releasable attaching means is a hook and loop fastener overlying the CMC joint between the dorsum and palm of the patient.

12. The restriction splint as recited in claim 1 wherein an open ended sleeve member is connected with said splint body at the forward end thereof and configured for receiving the thumb of the patient.

13. A method for inmmobilizing the CMC joint in the hand of a patient, comprising the steps of; wrapping the hand of the patient in a splint body encircling and overlying the palm and dorsum of the patient; controlling said wrapping to effect compressive engagement between said splint body and said CMC joint; tensioning a strap member having a fixed end connected to said splint body over the exterior surface of said splint body adjacent said CMC joint for applying compression thereto; extending a free end of said strap member forwardly over palm and rearwardly through the web between the thumb and the index finger of the patient; attaching said free end to said splint body with sufficient tension to immobilize said CMC joint.

14. The method as recited in claim 13 including a width for said strap member in the area overlying the web sufficient to orient the thumb a spaced, immobilized position from the index finger of the patient.

15. The method as recited in claim 14 wherein including bidirectionally tensioning the body over the CMC joint and applying light compression thereto for alleviating pain.

16. The method as recited in claim 15 including providing a sleeve member on said body for receiving the thumb of the patient and overlying the web between the thumb and the index finger of the patient.

* * * * *